(12) United States Patent
Cao et al.

(10) Patent No.: US 6,620,983 B1
(45) Date of Patent: Sep. 16, 2003

(54) SYNTHESIS OF ALUMINOPHOSPHATES AND SILICOALUMINOPHOSPHATES

(75) Inventors: Guang Cao, Branchburg, NJ (US); Matu J. Shah, Livingston, NJ (US); Karl G. Strohmaier, Port Murray, NJ (US); Richard B. Hall, Whitehouse Station, NJ (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 0 days.

(21) Appl. No.: 10/171,186

(22) Filed: Jun. 12, 2002

(51) Int. Cl.$^7$ .............................. B01J 29/83; B01J 29/85
(52) U.S. Cl. ................... 585/640; 585/639; 502/208; 502/214; 423/305; 423/306; 423/327.1; 423/DIG. 30
(58) Field of Search .................... 423/302, 304, 423/305, 306, 327.1, DIG. 30; 502/208, 214; 585/638, 639, 640

(56) References Cited

U.S. PATENT DOCUMENTS

| | | | |
|---|---|---|---|
| 4,310,440 A | 1/1982 | Wilson et al. | 252/435 |
| 4,440,871 A | 4/1984 | Lok et al. | 502/214 |
| 4,503,023 A | 3/1985 | Breck et al. | 423/328 |
| 4,786,487 A | 11/1988 | Kuehl | 423/306 |
| 4,861,739 A | 8/1989 | Pellet et al. | 502/64 |
| 5,000,931 A * | 3/1991 | Gortsema et al. | 423/305 |
| 5,096,684 A | 3/1992 | Guth et al. | 423/306 |
| 5,932,512 A * | 8/1999 | Sun | 502/214 |
| 6,001,328 A | 12/1999 | Lillerud et al. | 423/718 |
| 6,162,415 A | 12/2000 | Liu et al. | 423/706 |

FOREIGN PATENT DOCUMENTS

| | | | |
|---|---|---|---|
| CN | 1067633 | 6/1993 | B01J/29/02 |
| EP | 0 391 774 | 10/1990 | C01B/33/34 |
| EP | 993 867 | 9/2000 | |
| FR | 2 682 944 | 4/1993 | C01B/25/36 |
| WO | WO 97/33692 | 9/1997 | B01J/29/04 |
| WO | WO 98/15496 | 4/2000 | |

OTHER PUBLICATIONS

"Synthesis characterization and Rietveld refinement of the tetragonal varient of ALPO4–16 prepared in fluride medium," Scho Darie, C., Patarin, J., Le Goff, P.Y., Kessler, H., and Benazzi, E., Microporous Materials, Sep. 1994, pp. 123–132.*

"The opportunities of the fluoride route in the synthesis of microporous materials," Kessler, H., Patarin, J., Schott–Darie, C., Stud. Surf. Sci. Catal. 85 (1994) pp. 75–113.*

Meier et al., "Atlas of Zeolite Framework Types," Fifth Revised Edition, p. 96 (2001).

E. H. Halvorsen, "Synthesis and Characterization of Aluminophosphate Molecular Sieve" Ph.D. Thesis, University of Oslo, (1996).

Wilson et al., "The Characteristics of SAPO–34 which Influence the Conversion of Methanol to Light Oelfins," *Microporous and Mesoporous Materials*, vol. 29, pp. 117–126, (1999).

Vistad et al., "Multinuclear NMR Analysis of Sapo–34 Gels in the Presence and Absence of HF: The Initial Gel", *Journal of Physical Chemistry A.*, 103, pp. 2540–2552 (1990).

Kwon et al., "Synthesis of Mesoporous Molecular Sieves Hydrolysis of H2SiF6 by a Non–ionic Polyethyleneoxide Surfactant Template," Microporous and Mesoporous Materials, vol. 27 pp. 255–259 (1999).

McKie et al., "Essentials of Crystallography", Blackwell Scientific Publications, p. 89 (1986).

Feng et al., *Amine–directed Syntheses and Crystal Structures of Phosphate–based Zeolite Analogs, Microporous and Mesoporous Materials*, vol. 23, pp. 221–229 (1998).

H. Kessler, *Synthesis in the Presence of Fluoride High–Silica Zeolites, Aluminophosphates and Derived Materials, Microporous Materials*, vol. 22 pp. 5–17–518, (1998).

Prakash et al., *Synthesis and Characterization of SAPO–5 Molecular Sieve Using N, N–dimethylbenzylamine as Template, Microporous Materials*, vol. 2, pp. 83–89, (1994).

Harding et al., *Microcrystal Structure Determination of AlPO$_4$–CHA Using Synchrotron Radiation, Acta Cryst.*, vol. C50, pp. 852–854, (1994).

* cited by examiner

*Primary Examiner*—Tom Dunn
*Assistant Examiner*—Christina Ildebrando
(74) *Attorney, Agent, or Firm*—Jaimes Sher

(57) ABSTRACT

The invention is directed to a method of synthesizing aluminophosphate or silicoaluminophosphate molecular sieves and in particular to the synthesis of silicoaluminophosphate molecular sieves using synthesis templates in combination with a source of fluoride comprising at least two fluoride substituents. The use of such fluorine containing compounds results in good quality low silica SAPO molecular sieves of CHA framework type.

41 Claims, 2 Drawing Sheets

US 6,620,983 B1

SYNTHESIS OF ALUMINOPHOSPHATES AND SILICOALUMINOPHOSPHATES

FIELD OF INVENTION

This invention relates to the synthesis of aluminophosphate and silico-aluminophosphate molecular sieves, to aluminophosphate and silico-aluminophosphates having the CHA framework type and their use. In particular the present invention relates to the synthesis of aluminophosphate and silico-aluminophosphate molecular sieves using synthesis templates in combination with compounds, which have two or more fluorine substituents as a source of fluoride ions.

BACKGROUND OF THE INVENTION

Olefins are traditionally produced from petroleum feedstock by catalytic or steam cracking processes. These cracking processes, especially steam cracking, produce light olefin(s) such as ethylene and/or propylene from a variety of hydrocarbon feedstocks. It has been known for some time that oxygenates, especially alcohols, e.g. methanol, are convertible into light olefin(s). The preferred methanol conversion process is generally referred to as methanol-to-olefin(s) (MTO) process, where methanol is converted to primarily ethylene and propylene in the presence of a molecular sieve.

Some of the most useful molecular sieves for converting methanol to olefin(s) are the metalloaluminophosphates such as the silicoaluminophosphates (SAPO's). There are a wide variety of SAPO molecular sieves known in the art, of these the more important examples include SAPO-5, SAPO-11, SAPO-18, SAPO-34, SAPO-35, SAPO-41, and SAPO-56. For the methanol-to-olefins process SAPO molecular sieves having the CHA framework and especially SAPO-34 are particularly important catalysts. The CHA framework type has a double six-ring structure in an ABC stacking arrangement. The pore openings of the structure are defined by eight member rings that have a diameter of about 4.0 Å, and cylindrical cages within the structure of approximately 10×6.7 Å type ("Atlas of Zeolite Framework Types", 2001, 5th Edition, p. 96). Other SAPO molecular sieves of CHA framework type include SAPO-44, SAPO-47 and ZYT-6.

The synthesis of $AlPO_4$ and SAPO molecular sieves is a complicated process. There are a number of variables, which need to be controlled in order to optimise the synthesis in terms of the purity, yield, and quality of the molecular sieve produced. Of these variables the choice of template (hereinafter also referred to as templating agent) is usually one of the most important in determining which framework type is obtained.

One desirable group of silicoaluminophosphate molecular sieves are those that have low silicon contents. Silicoaluminophosphates of the CHA framework type with low silicon contents are particularly desirable for use in the methanol-to-olefins process. Wilson, et al., reported that it is beneficial to have lower Si content for methanol-to-olefins reaction (*Microporous and Mesoporous Materials*, 29, 117–126, 1999). Low Si content has the effect of reducing propane formation and decreasing catalyst deactivation.

In U.S. Pat. No. 4,440,871 (Lok et.al) the synthesis of a wide variety of SAPO materials of various framework types are described with a number of specific examples. Also disclosed are a large number of possible organic templates, with some specific examples. In the specific examples a number of CHA framework type materials are described. The preparation of SAPO-34 is reported, using tetraethylammonium hydroxide (TEAOH), or isopropylamine, or mixtures of TEAOH and dipropylamine (DPA) as templates. Also disclosed in this patent is a specific example that utilises cyclohexylamine in the preparation of SAPO-44. Although other template materials are described in this patent there are no other templates indicated as being suitable for preparing SAPO's of CHA framework type. Certain aminoalcohols are mentioned, including triethanolamine, N-methyldiethanolamine, N-methylethanolamine, N,N-dimethylethanolamine and N,N-diethylethanolamine as possible templates for SAPO molecular sieves. Of these materials N,N-diethylethanolamine is shown to produce SAPO-5, which is of framework type AFI. For the other aminoalcohols no indication is provided as to which SAPO or which framework type may be obtained through their use.

Since the synthesis of SAPO-34 was reported in U.S. Pat. No. 4,440,871, tetraethylammonium hydroxide (TEAOH) either alone, or in combination with dipropylamine (DPA), has been the preferred template for preparing SAPO-34. However, there are problems associated with the use of TEAOH and DPA. When used alone, TEAOH affords a limited range of synthesis parameters. For example, under certain conditions TEAOH will also template the synthesis of SAPO-18 which has the AEI framework type. TEAOH is thus relatively intolerant to synthesis condition variations. TEAOH is sometimes combined with DPA. However, DPA has a low boiling point (110° C.) resulting in the need for production plants that can handle high pressures. In certain countries, the use of DPA requires special regulatory authorizations due to its toxicity. Also, DPA is an aggressive template and is often implicated in re-dissolution of the silicoaluminophosphate molecular sieve during its synthesis, resulting in poor quality crystalline product due to surface pitting of the crystals. Finally, it has proved difficult up to now to make pure phase CHA silicoaluminophosphate molecular sieves with a low silica to alumina ratio.

In U.S. Pat. No. 4,440,871, it was reported that SAPO-44 was obtained "as the major phase" using cyclohexylamine as a template. In U.S. Pat. No. 6,162,415 (Liu, et.al.), relatively pure CHA SAPO-44 was obtained using the same template but with control of the ratio of template to aluminium source and the ratio of phosphorous source to aluminium source.

In European Patent Publication No. 0,993,867, it was reported that the use of methylbutylamine resulted in SAPO-47 and the use of cyclohexylamine resulted in impure SAPO-44. Methylbutylamine has an even lower boiling point, at 91° C., than DPA.

In U.S. Pat. No. 4,861,739 (Pellet, et al.), Example 102, it was reported that the use of N,N-diethylethanolamine produced CoAPSO-47, having Si concentrated on the peripheries of the crystal and Co at the centre.

In U.S. Pat. No. 4,310,440 (Wilson et.al), triethanolarnine, N,N-dimethylethanolamine, N,N-diethylethanolamine, N-methyldiethanolamine, and N-methylethanolamine, were all used to prepare $AlPO_4$-5, aluminophosphates of framework type AFI. N-methylethanolamine was also reported to produce $AlPO_4$-21 of framework type AWO.

In European Patent Publication No. 0,993,867, it was reported that diethanolamine produced SAPO-34 and SAPO-5 under different synthesis conditions.

In the art various attempts have been made to improve the synthesis of $AlPO_4$ or SAPO molecular sieves. One approach has been the addition of a source of fluoride ions to the synthesis mixture.

In U.S. Pat. No. 5,096,684 (Guth et.al.), morpholine and tetraethylammonium hydroxide were found to template the production of SAPO-34 when in the presence of HF. According to Guth et.al. the use of HF in combination with the organic template results in silicoaluminophosphates which have improved thermal and hydrolytic stability.

The use of morpholine in combination with hydrogen fluoride has also been described in: "Multinuclear NMR Analysis of SAPO-34 Gels in the Presence and Absence of HF: The Initial Gel", O. B. Vistad, E. W. Hansen, D. E. Akporiaye, K. P. Lillerud: J. Phys. Chem A 103 (1999) 2540–2552.

In U.S. Pat. No. 4,786,487 (Kuehl et.al.), SAPO-20 was produced from synthesis mixtures containing tetramethylammonium hydroxide and fluoride ions from water soluble sources of fluoride such as Na, K and ammonium fluoride.

In U.S. Pat. No. 6,001,328 (Lillerud et.al.), silicoaluminophosphate indicated as UiO-S7 was prepared using tetramethylammonium hydroxide pentahydrate or tetramethylammonium hydroxide in combination with HF.

In a Ph.D. thesis (E. H. Halvorsen, University of Oslo, 1996), it was reported that low silica SAPO-34, designated as UiO-S4, was produced using TEAOH template in combination with HF.

In U.S. Pat. No. 4 503 023 $[NH_4]_2SiF_6$ is used to post-treat zeolites in order to increase the Si/Al ratio in the zeolite structure. In this case the reagent is used as a source of Si, which substitutes framework aluminum.

Hexafluorosilicic acid, $H_2SiF_6$, has been used as a source of Si for the synthesis of zeolite and mesoporous molecular sieves. See, for example, *Microporous and Mesoporous Materials*, 1999, 27 (2–3), 255–259, Kwon, et al.

As can bee seen from the disclosures described herein, there have been a number of attempts to find alternative synthesis templates for the molecular sieves having the CHA framework type with limited success. It is desirable therefore to find new templates, which are specific for the synthesis of molecular sieves having the CHA framework type. In addition there is a need for new templating systems which afford more effective control of the final composition of the SAPO molecular sieve materials and in particular those that can produce final products with low silica that are relatively pure. A further need is to find methods of preparing low silica SAPO molecular sieves, which do not require the use of hydrogen fluoride, which is toxic, corrosive and volatile.

In the present invention some or all of these requirements have been met by the use of specific fluorine containing compounds that have two or more fluorine substituents, as the source of fluoride ion, in the synthesis of aluminophosphates or silicoaluminophosphates. These sources of fluoride are as effective as hydrogen fluoride but are much easier to handle in the process and provide SAPO's with the CHA framework type.

BRIEF DESCRIPTION OF THE DRAWINGS

The present invention will be better understood by reference to the Detailed Description of the Invention when taken together with the attached drawings wherein.

SUMMARY OF THE INVENTION

Figure 1:
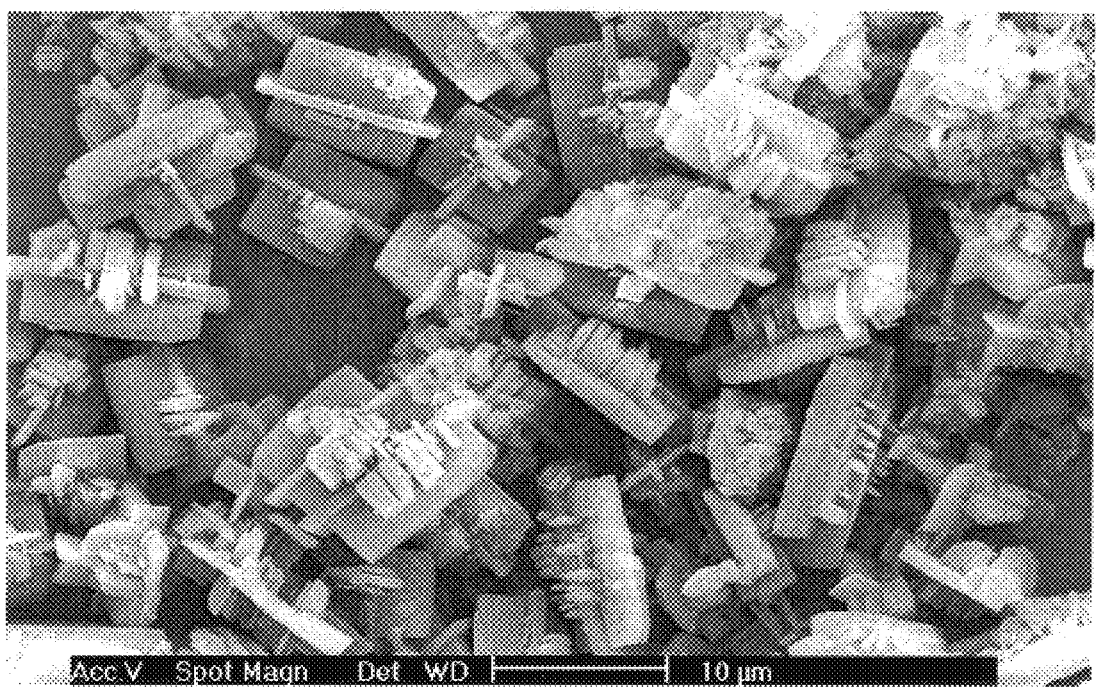
FIG. 1 shows a Scanning Electron Micrograph of twinned crystals.

The present invention provides a method for preparing aluminophosphate or silicoaluminophosphate molecular sieves, which process comprises;

a. forming a reaction mixture comprising a source of aluminum, a source of phosphorus, at least one organic template, at least one compound which comprises two or more fluorine substituents and capable of providing fluoride ions, and, optionally, a source of silicon, and b. inducing crystallization of aluminophosphate or silicoaluminophosphate molecular sieve from the reaction mixture.

Preferably, the aluminophosphate or silicoaluminophosphates made by the method of the present invention have the CHA framework type. An XRD of the aluminophosphates or silicoaluminophosphates after calcination is that of a molecular sieve of the CHA framework type.

In a further aspect the present invention provides a crystalline aluminophosphate or silicoaluminophosphate molecular sieve comprising within its intra-crystalline structure fluoride and at least one organic template and which crystalline molecular sieve has a twinned morphology. In a preferred embodiment the organic template contains one or more N,N-dialkylamino moieties, preferably one or more N,N-dimethylamino moieties.

In another embodiment the present invention provides a method for the manufacture of a molecular sieve catalyst composition, which method comprises forming a mixture comprising at least one aluminophosphate or low silica silicoaluminophosphate molecular sieve comprising within its intra-crystalline structure fluoride and at least one organic template and which crystalline molecular sieve has a twinned morphology, with at least one formulating agent. In yet another embodiment, the present invention provides a method for the manufacture of a molecular sieve catalyst composition, which method comprises forming a mixture comprising at least one molecular sieve as obtained from a synthesis method utilising a template in combination with at least one compound which comprises two or more fluorine substituents and is capable of providing fluoride ions, with at least one formulating agent.

In yet a further embodiment the present invention provides for a molecular sieve catalyst composition comprising at least one aluminophosphate or low silica silicoaluminophosphate molecular sieve comprising within its intra-crystalline structure fluoride and at least one organic template and which crystalline molecular sieve has a twinned morphology. In another embodiment, the present invention provides for a molecular sieve catalyst composition comprising at least one molecular sieve as obtained from a synthesis method utilising a template in combination with at least one compound which comprises two or more fluorine substituents and is capable of providing fluoride ions, in admixture with at least one formulating agent.

In a further embodiment the present invention provides for the use of at least one compound, which comprises two or more fluorine substituents and is capable of providing fluoride ions, as a source of fluoride ions in the synthesis of aluminophosphate or low silica silicoaluminophosphates of CHA framework type.

The present invention also relates to new morphological form of SAPO molecular sieve of the CHA framework type. This form is a twinned morphology. Twinning refers to co-joined crystals of the same kind in some definite, mutual orientation (*Essentials of Crystallography* by Duncun Mckie and Christine McKie, Blackwell Scientific Publications, Oxford, 1986. P89.) Thus, in a further embodiment the present invention also provides for a silicoaluminophosphate of CHA framework type, which comprises a twinned morphology.

The SAPO materials of the present invention are particularly effective as catalysts or catalyst components in oxygenates and hydrocarbon conversion processes and in particular in the conversion of oxygenates to olefins. Therefore, the present invention in a further embodiment, also provides for an oxygenate or hydrocarbon conversion process comprising the steps of:

(a) introducing a feedstock to a reactor system in the presence of a silicoaluminophosphate of the CHA framework type, which comprises a twinned morphology;

(b) withdrawing from the reactor system an effluent stream; and (c) passing the effluent gas through a recovery system recovering at least the one or more conversion products.

DETAILED DESCRIPTION OF THE INVENTION

Introduction

The invention is primarily directed toward a method for synthesising aluminophosphates (AlPO's) and silicoaluminophosphates (SAPO's) of the CHA framework type. In particular it has been found that a specific group of fluorine containing compounds that comprise two or more fluorine substituents and are capable of providing fluoride ions, are effective in combination with organic templates, in the manufacture of aluminophosphates and low silica silicoaluminophosphates of the CHA framework type. It is also possible to utilise this combination with other known templates for the synthesis of SAPO's having the CHA framework type in a dual template synthesis to produce low acidity SAPO's having the CHA framework type. In particular they may be utilised with tetraethylammoniumhydroxide in place of DPA. The specific fluorine containing compounds have been found to be particularly effective when used in combination with templates, which contain N,N,-dialkyl amino moieties.

Molecular Sieves

The AlPO or SAPO molecular sieves of the present invention may be represented by the empirical formula, on an anhydrous basis:

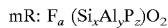

mR: $F_a$ $(Si_xAl_yP_z)O_2$ wherein R represents at least one templating agent; m is the number of moles of R per mole of $(Si_xAl_yP_z)O_2$ and m has a value from 0.0417 to 0.3333, preferably 0.0833 to 0.25, and most preferably from 0.125 to 0. 1667; x, y, and z respectively represent the mole fraction of Si, Al and P as tetrahedral oxides. F indicates fluoride ion and "a" is the number of moles of F per mole of $(Si_xAl_yP_z)O_2$; a has a value between 0.001 to 0.167. For AlPO molecular sieves, x is zero.

In an embodiment, m is greater than or equal to 0.05, and x is less than or equal to 0.2, y and z are greater than or equal to 0.01. In another embodiment, m is in the range of greater than 0.01 to about 0.4, x is less than or equal to 0.1, y is in the range of from 0.4 to 0.7, and z is in the range of from 0.25 to 0.9, more preferably m is in the range of from 0.08 to 0.25, x is less than or equal to 0.08, y is in the range of from 0.4 to 0.6, and z is in the range of from 0.3 to 0.5. Preferably, when the molecular sieve is a SAPO, x is greater or equal to 0.01.

Prior to calcination, the molecular sieves of the invention substantially have the CHA framework type: the XRD patterns of the assynthesized molecular sieves provide no immediate indication that these materials have the CHA framework type. However, when the molecular sieves are calcined, the resulting AlPO's or SAPO's have an XRD pattern typical of the CHA framework type and are of high purity in terms of their framework type. The molecular sieves prepared according to the present invention have little or no intergrowth with other molecular sieve framework type.

Molecular Sieve Synthesis

Generally, aluminophosphate and silicoaluminophosphate molecular sieves are synthesized by the hydrothermal crystallization of one or more of a source of aluminium, a source of phosphorous, a source of silicon for silicoaluminophosphate, and a templating agent.

In the process of the present invention there is the requirement to include at least one compound, which comprises two or more fluorine substituents.

Typically, in the method of the present invention a combination of a source of aluminium, a source of phosphorous, one or more templating agents, a source of fluoride, and, optionally, one or more metal containing compounds are placed in a sealed pressure vessel, optionally lined with an inert plastic such as polytetrafluoroethylene, and heated, under a crystallization pressure and temperature, until a crystalline material is formed, and then recovered by filtration, centrifugation and/or decanting.

In a typical synthesis of the molecular sieve, the phosphorous-, aluminium-, and optionally silicon- containing components are mixed, preferably while stirring and/or agitation and/or seeding with a crystalline material, optionally with an alkali metal, in a solvent such as water, and one or more templating agents, to form a synthesis mixture. To this synthesis mixture or gel is added the fluorine-containing compound. This mixture or gel is then heated under crystallization conditions of pressure and temperature as described in U.S. Pat. Nos. 4,440,871, which is fully incorporated by reference.

Suitable templates for use in the process of the present invention for the manufacture of low silica SAPO of the CHA framework type may be selected from: the group of tetraethylammonium compounds, such as tetraethyl ammonium hydroxide (TEAOH), tetraethyl ammonium phosphate, tetraethyl ammonium fluoride, tetraethyl ammonium bromide, tetraethyl ammonium chloride and tetraethyl ammonium acetate and also include DPA, isopropylamine, cyclohexylamine, methylbutylamine, morpholine, diethanolamine, and triethylamine or mixtures of two or more of these conventional templates, in particular the mixture of TEAOH and DPA.

In addition templates may be used which would not normally be expected to produce SAPO molecular sieves of the CHA framework type. Such templates include templates comprising one or more N,N-dialkylamino moieties. In a preferred embodiment, the template has the following general structure:

$R^1R^2N—R^3$, wherein $R^1$ and $R^2$ are independently selected from the group consisting of linear or branched alkyl groups having from 1 to 5 carbon atoms and $R^3$ is selected from the group consisting of linear or branched alkyl groups having from 1 to 12 carbon atoms, cycloalkyl groups having from 1 to 8 carbon atoms, linear or branched alcohols having from 1 to 12 carbon atoms, linear or branched amine-containing groups having from 1 to 12 carbon atoms. Preferably, $R^1$ and $R^2$ are independently selected from the group consisting of methyl, ethyl, n-propyl and i-propyl, n-butyl and its branched isomers, n-pentyl and its branched isomers. Most preferably, $R^1$ and $R^2$ are both methyl groups. Preferably, $R^3$ is selected from the group consisting of methyl, ethyl, n-propyl and i-propyl, n-butyl and its branched isomers, n-pentyl and its branched isomers, n-hexyl and its branched isomers, n-heptyl and its branched isomers, and all these alkyl groups substitutes by one or several OH or $NH_2$ groups.

The most preferred templates comprising N,N-dialkylamino moieties have the following general structure:

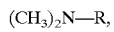

wherein R is a substituted or un-substituted aliphatic or cycloaliphatic group. R may be a linear or branched alkyl group, or a linear or branched alcohol or a linear or branched amine-containing group. Preferably, R contains an alkyl group of from 1 to 12 carbon atoms, more preferably 1 to 10 carbon atoms, and most preferably 1 to 8 carbon atoms.

In a more preferred embodiment the template is a selected from one or more of the following N,N-dimethylamino compounds: N,N-dimethylethanolamine (DMEA), N,N-dimethylpropanolamine, N,N-dimethylbutanolamine, N,N-dimethylheptanolamine, N,N-dimethylhexanolamine, N,N-dimethylethylenediamine, N,N-dimethylpropyelenediamine, N,N-dimethylbuytlenediamine, N,N-dimethylheptylenediamine, N,N-dimethylhexylenediamine 1-dimethylamino-2-propanol, or dimethylethylamine, dimethylpropylamine, dimethylheptylamine or dimethylhexylamine. More preferably the template is selected from one or more of the following N,N-dimethylamino compounds: N,N-dimethylethanolamine, N,N-dimethylpropanolamine, or N,N-dimethyl- propyelenediamine. Most preferably the template is N,N-dimethylethanolamine or N,N-dimethylpropylenediamine.

In a further embodiment the template comprising one or more dialkylamino moieties may be used in combination with one or more conventional templates as described above. When these additional templates are used in combination with templates comprising one or more dialkylamino moieties, it is possible to produce silicoaluminophosphates of the CHA framework type, which have a new morphology, and in particular a twinned morphology. Particularly preferred in this regard is the combination of morpholine and DMEA.

The preferred combination of templates is DMEA with or without morpholine, in combination with the fluorine-containing compound.

The template should be used at a template/$Al_2O_3$ mole ratio of 1 or greater. When DMEA is the template and it is required that the final product be free of amorphous material, then ideally DMEA must be used in a ratio of greater than 1 DMEA/$Al_2O_3$. At ratios of 1 or less it has been found that, although the crystalline molecular sieve is XRD pure, there are small amounts of amorphous material present which may be undesirable. Preferably the mole ratio of template/$Al_2O_3$ is within the range of 1.5 to 3.0, more preferably 1.5 to 2.0.

The use of the fluorine containing compounds of the present invention results in the production of low silica content SAPO molecular sieves of the CHA framework type. By low silica is meant that there is 1 or less than 1 silicon atoms present per 12 T-atoms which constitute a CHA cage. It is preferred that the number of Si per cage is less than 1. In terms of Si/Al ratio, by low silica is meant that the Si/Al atomic ratio is less than 0.167.

In one preferred embodiment, when a templating agent is used in the synthesis of a molecular sieve, it is preferred that the templating agent is substantially, preferably completely, removed after crystallization by numerous well known techniques, for example, heat treatments such as calcination. Calcination involves contacting the molecular sieve containing the templating agent with a gas, preferably containing oxygen, at any desired concentration at an elevated temperature sufficient to either partially or completely decompose and oxidize the templating agent.

In one embodiment, the calcined molecular sieve has a Si/Al ratio less than 0.50, preferably less than 0.33, more preferably less than 0.17, and most preferably less than 0.10.

Suitable fluorine containing compounds for use in the present invention have at least two fluorine substituents and are capable of being source of fluoride. Ideally they are compounds that are easily hydrolysed under the normal synthesis conditions used for the manufacture of alumino- and silicoaluminophosphates. In this context they will be compounds which are hydrolysed at pH of <9 or at temperatures of greater than 50° C. or both. Examples of suitable compounds include [$(C_2H_5)_4N$] $PF_6$, $NaHF_2$, $HPF_6$ $NH_4PF_6$, $H_2SiF_6$, $(NH_4)_2SiF_6$, $NH_4HF_2$, $NaPF_6$, $AlF_3$ (anhydrous or hydrate), $(NH_4)_3AlF_6$, $(NH_4)_2TiF_6$, $(NH_4)_2ZrF_6$, $(NH_4)_2GeF_6$, $(NH_4)_2SnF_6$. The fluorid source is preferably selected from $(NH_4)_2SiF_6$, $NH_4HF_2$, $HPF_6$, $H_2SiF_6$, $AlF_3$ (anhydrous or hydrate), $NH_4PF_6$, $NaPF_6$, more preferably $(NH_4)_2SiF_6$, $HPF_6$, $H_2SiF_6$, $AlF_3$ (anhydrous or hydrate), $NH_4PF_6$.

The use of $NaHF_2$ can dramatically slow down the crystallization, possibly due to the presence of Na. $(NH_4)_2SiF_6$, whilst also being a potential source of silicon as well as fluoride, may require greater control during use as its order of addition may effect the composition of the final product. The use of $(NH_4)HF_2$ sometimes results in the simultaneous production of non-porous $AlPO_4$-15, which is not desirable. However, certain levels of $AlPO_4$-15 may be tolerated as this material is substantially inert under methanol-to-olefin conditions. The preferred fluorine containing compound is $HPF_6$ as it is effective and does not have similar problems to those identified for some of the fluorine containing compounds discussed above. The fluorine containing material (FCM) should be used at a mole ratio of FCM/$Al_2O_3$ of 0.01 or greater, preferably 0.02 or greater and most preferably 0.035 or greater. Ideally, it is within the range of 0.01 to 0.5, preferably 0.02 to 0.25, and most preferably 0.035 to 0.15.

When $(NH_4)_2SiF_6$ is used as the source of fluorine the order of its addition during formation of the pre-crystallization gel is important. If this material is added first then the resultant product may have 50% or less of the silicon present compared to when this compound is added as the last ingredient in the gel formation prior to crystallization. For the preparation of low silica SAPOs, it is thus preferred that the source of $SiF_6^-$ be introduced as the first component during manufacture of the pre-crystallization gel. However, to maximize silicon incorporation in the molecular sieve, it is preferred that the source of $SiF_6^-$ be introduced as the last component during manufacture of the pre-crystallization gel.

It has been further observed that when the temperature of crystallization is lowered the resultant low silica SAPO molecular sieve materials of the CHA framework type have reduced crystallite size. Thus, when a temperature of 160° C.

or greater is used in combination with N,N-dimethylethanolamine as the template and $NH_4PF_6$ as the fluorine containing compound, large crystals of material are produced typically with sizes up to 10–15 ptm. If the temperature is dropped below 160° C. e.g. 150° C. or below, then the particle size is typically less than 5 μm and largely consists of particles in the 2–3 μm. At the lower temperature range there is a narrower particle size distribution.

If the process for the manufacture of low silica SAPO's of the CHA framework type is carefully controlled it is possible to obtain new morphological forms. In this aspect it is important to utilise a mixed template system in combination with the fluorine containing material. The resultant product has a twinned morphology. Twinning refers to co-joined crystals of the same kind in some definite, mutual orientation.

In a further aspect the process for the manufacture of low silica SAPO of CHA framework type may utilise one or more modifying agents, which are typically surfactant materials. Of particular interest are the cationic surfactants such as n-$C_{16}H_{33}N(CH_3)_3{}^+Cl^-$(TMCA$^+$ Cl$^-$). When these surfactant are used at low levels e.g. 0.1 wt % or less, preferably 0.05 wt % or less, they result in a reduced crystallite size and change of crystal morphology of the molecular sieve.

Method for Making Molecular Sieve Catalyst Compositions

The molecular sieves of the present invention may be combined with one or more formulating agents, to form a molecular sieve catalyst composition or a formulated molecular sieve catalyst composition. The formulating agents may be one or more materials selected from the group consisting of binding agents, matrix or filler materials catalytically active materials and mixtures thereof This formulated molecular sieve catalyst composition is formed into useful shape and sized particles by well-known techniques such as spray drying, pelletizing, extrusion, and the like.

There are many different binders that are useful in forming the molecular sieve catalyst composition. Non-limiting examples of binders that are useful alone or in combination include various types of hydrated alumina, silicas, and/or other inorganic oxide sol. One preferred alumina containing sol is aluminium chlorhydrol. The inorganic oxide sol acts like glue binding the synthesized molecular sieves and other materials such as the matrix together, particularly after thermal treatment. Upon heating, the inorganic oxide sol, preferably having a low viscosity, is converted into an inorganic oxide matrix component. For example, an alumina sol will convert to an aluminium oxide matrix following heat treatment.

Aluminium chlorhydrol, a hydroxylated aluminium based sol containing a chloride counter ion, has the general formula of $Al_mO_n(OH)_oCl_p.x(H_2O)$ wherein m is 1 to 20, n is 1 to 8, o is 5 to 40, p is 2 to 15, and x is 0 to 30. In one embodiment, the binder is $Al_{13}O_4(OH)_{24}Cl_7.12(H_2O)$ as is described in G. M. Wolterman, et al., Stud. Surf. Sci. and Catal., 76, pages 105–144 (1993), which is herein incorporated by reference. In another embodiment, one or more binders are combined with one or more other non-limiting examples of alumina materials such as aluminium oxyhydroxide, γ-alumina, boehmite, diaspore, and transitional aluminas such as α-alumina, β-alumina, γ-alumina, δ-alumina, ε-alumina, κ-alumina, and ρ-alumina, aluminium trihydroxide, such as gibbsite, bayerite, nordstrandite, doyelite, and mixtures thereof.

In another embodiment, the binders are alumina sols, predominantly comprising aluminium oxide, optionally including some silicon. In yet another embodiment, the binders are peptised alumina made by treating alumina hydrates such as pseudobohemite, with an acid, preferably an acid that does not contain a halogen, to prepare sols or aluminium ion solutions. Non-limiting examples of commercially available colloidal alumina sols include Nalco 8676 available from Nalco Chemical Co., Naperville, Ill., and Nyacol available from The PQ Corporation, Valley Forge, Pa.

The molecular sieve of the present invention may be combined with one or more matrix material(s). Matrix materials are typically effective in reducing overall catalyst cost, act as thermal sinks assisting in shielding heat from the catalyst composition for example during regeneration, densifying the catalyst composition, increasing catalyst strength such as crush strength and attrition resistance, and to control the rate of conversion in a particular process.

Non-limiting examples of matrix materials include one or more of the following: rare earth metals, metal oxides including titania, zirconia, magnesia, thoria, beryllia, quartz, silica or sols, and mixtures thereof, for example silica-magnesia, silica-zirconia, silica-titania, silica-alumina and silica-alumina-thoria. In one embodiment, matrix materials are natural clays such as those from the families of montmorillonite and kaolin. These natural clays include sabbentonites and those kaolins known as, for example, Dixie, McNamee, Georgia and Florida clays. Non-limiting examples of other matrix materials include: haloysite, kaolinite, dickite, nacrite, or anauxite. In one embodiment, the matrix material, preferably any of the clays, are subjected to well known modification processes such as calcination and/or acid treatment and/or chemical treatment.

In one preferred embodiment, the matrix material is a clay or a clay-type composition, preferably the clay or clay-type composition having a low iron or titania content, and most preferably the matrix material is kaolin. Kaolin has been found to form a pumpable, high solid content slurry; it has a low fresh surface area, and it packs together easily due to its platelet structure. A preferred average particle size of the matrix material, most preferably kaolin, is from about 0.1 μm to about 0.6 μm with a D90 particle size distribution of less than about 1 μm.

In one embodiment, the binder, the molecular sieve and the matrix material are combined in the presence of a liquid to form a molecular sieve catalyst composition, where the amount of binder is from about 2% by weight to about 30% by weight, preferably from about 5% by weight to about 20% by weight, and more preferably from about 7% by weight to about 15% by weight, based on the total weight of the binder, the molecular sieve and matrix material, excluding the liquid (after calcination).

In another embodiment, the weight ratio of the binder to the matrix material used in the formation of the molecular sieve catalyst composition is from 0:1 to 1:15, preferably 1:15 to 1:5, more preferably 1:10 to 1:4, and most preferably 1:6 to 1:5. It has been found that a higher sieve content, lower matrix content, increases the molecular sieve catalyst composition performance, however, lower sieve content, higher matrix material, improves the attrition resistance of the composition.

Upon combining the molecular sieve and the matrix material, optionally with a binder, in a liquid to form a slurry, mixing, preferably rigorous mixing is needed to produce a substantially homogeneous mixture containing the molecular sieve. Non-limiting examples of suitable liquids include one or a combination of water, alcohol, ketones, aldehydes, and/or esters. The most preferred liquid is water. In one embodiment, the slurry is colloid-milled for a period of time sufficient to produce the desired slurry texture, sub-particle size, and/or sub-particle size distribution.

The molecular sieve and matrix material, and the optional binder, may be in the same or different liquid, and may be combined in any order, together, simultaneously, sequentially, or a combination thereof. In the preferred embodiment, the same liquid, preferably water is used. The molecular sieve, matrix material, and optional binder, are combined in a liquid as solids, substantially dry or in a dried form, or as slurries, together or separately. If solids are added together as dry or substantially dried solids, it is preferable to add a limited and/or controlled amount of liquid.

In one embodiment, the slurry of the molecular sieve, binder and matrix materials is mixed or milled to achieve a sufficiently uniform slurry of sub-particles of the molecular sieve catalyst composition that is then fed to a forming unit that produces the molecular sieve catalyst composition. In a preferred embodiment, the forming unit is spray dryer. Typically, the forming unit is maintained at a temperature sufficient to remove most of the liquid from the slurry, and from the resulting molecular sieve catalyst composition. The resulting catalyst composition when formed in this way takes the form of microspheres.

When a spray drier is used as the forming unit, typically, the slurry of the molecular sieve and matrix material, and optionally a binder, is co-fed to the spray drying volume with a drying gas with an average inlet temperature ranging from 200° C. to 550° C., and a combined outlet temperature ranging from 100° C. to about 225° C. In an embodiment, the average diameter of the spray dried formed catalyst composition is from about 40 μm to about 300 μm, preferably from about 50 μm to about 250 μm, more preferably from about 50 μm to about 200 μm, and most preferably from about 65 μm to about 90 μm.

During spray drying, the slurry is passed through a nozzle distributing the slurry into small droplets, resembling an aerosol spray into a drying chamber. Atomization is achieved by forcing the slurry through a single nozzle or multiple nozzles with a pressure drop in the range of from 100 psia to 1000 psia (690 kPaa to 6895 kPaa). In another embodiment, the slurry is co-fed through a single nozzle or multiple nozzles along with an atomisation fluid such as air, steam, flue gas, or any other suitable gas.

In yet another embodiment, the slurry described above is directed to the perimeter of a spinning wheel that distributes the slurry into small droplets, the size of which is controlled by many factors including slurry viscosity, surface tension, flow rate, pressure, and temperature of the slurry, the shape and dimension of the nozzle(s), or the spinning rate of the wheel. These droplets are then dried in a co-current or counter-current flow of air passing through a spray drier to form a substantially dried or dried molecular sieve catalyst composition, more specifically a molecular sieve in powder form.

Generally, the size of the powder is controlled to some extent by the solids content of the slurry. However, control of the size of the catalyst composition and its spherical characteristics are controllable by varying the slurry feed properties and conditions of atomisation.

In another embodiment, the formulated molecular sieve catalyst composition contains from about 1% to about 99%, more preferably from about 5% to about 90%, and most preferably from about 10% to about 80%, by weight of the molecular sieve based on the total weight of the molecular sieve catalyst composition.

In another embodiment, the weight percent of binder in or on the spray dried molecular sieve catalyst composition based on the total weight of the binder, molecular sieve, and matrix material is from about 2% by weight to about 30% by weight, preferably from about 5% by weight to about 20% by weight, and more preferably from about 7% by weight to about 15% by weight.

Once the molecular sieve catalyst composition is formed in a substantially dry or dried state, to further harden and/or activate the formed catalyst composition, a heat treatment such as calcination, at an elevated temperature is usually performed. A conventional calcination environment is air that typically includes a small amount of water vapour. Typical calcination temperatures are in the range from about 400° C. to about 1,000° C., preferably from about 500° C. to about 800° C., and most preferably from about 550° C. to about 700° C., preferably in a calcination environment such as air, nitrogen, helium, flue gas (combustion product lean in oxygen), or any combination thereof.

In one embodiment, calcination of the formulated molecular sieve catalyst composition is carried out in any number of well known devices including rotary calciners, fluid bed calciners, batch ovens, and the like. Calcination time is typically dependent on the degree of hardening of the molecular sieve catalyst composition and the temperature.

In a preferred embodiment, the molecular sieve catalyst composition is heated in nitrogen at a temperature of from about 600° C. to about 700C. Heating is carried out for a period of time typically from 30 minutes to 15 hours, preferably from 1 hour to about 10 hours, more preferably from about 1 hour to about 5 hours, and most preferably from about 2 hours to about 4 hours.

In addition to the molecular sieve of the present invention, the catalyst compositions of the present invention may comprise one or several other catalytically active materials. In one embodiment, one or several molecular sieves of the present invention are combined with one more of the following non-limiting examples of other catalytically active molecular sieves described in the following: Beta (U.S. Pat. No. 3,308,069), ZSM-5 (U.S. Pat. Nos. 3,702,886, 4,797, 267 and 5,783,321), ZSM-11 (U.S. Pat. No. 3,709,979), ZSM-12 (U.S. Pat. No. 3,832,449), ZSM-12 and ZSM-38 (U.S. Pat. No. 3,948,758), ZSM-22 (U.S. Pat. No. 5,336, 478), ZSM-23 (U.S. Pat. No. 4,076,842), ZSM-34 (U.S. Pat. No. 4,086,186), ZSM-35 (U.S. Pat. No. 4,016,245, ZSM-48 (U.S. Pat. No. 4,397,827), ZSM-58 (U.S. Pat. No. 4,698, 217), MCM-1 (U.S. Pat. No. 4,639,358), MCM-2 (U.S. Pat. No. 4,673,559), MCM-3 (U.S. Pat. No. 4,632,811), MCM-4 (U.S. Pat. No. 4,664,897), MCM-5 (U.S. Pat. No. 4,639, 357), MCM-9 (U.S. Pat. No. 4,880,611), MCM-10 (U.S. Pat. No. 4,623,527)MCM-14 (U.S. Pat. No. 4,619,818), MCM-22 (U.S. Pat. No. 4,954,325), MCM-41 (U.S. Pat. No. 5,098,684), M-41S (U.S. Pat. No. 5,102,643), MCM-48 (U.S. Pat. No. 5,198,203), MCM-49 (U.S. Pat. No. 5,236, 575), MCM-56 (U.S. Pat. No. 5,362,697), AlPO-11 (U.S. Pat. No. 4,310,440), titanium aluminosilicates (TASO), TASO-45 (EP-A-0 229, -295), boron silicates (U.S. Pat. No. 4,254,297), titanium aluminophosphates (TAPO) (U.S. Pat. No. 4,500,651), mixtures of ZSM-5 and ZSM-11 (U.S. Pat. No. 4,229,424), ECR-18 (U.S. Pat. No. 5,278,345).

In another embodiment, the molecular sieve of the present invention may be bound to another molecular sieve, as disclosed for example in the following: SAPO-34 bound AlPO4–5 (U.S. Pat. No. 5,972,203), PCT WO 98/57743 published Dec. 23, 1988 (molecular sieve and Fischer-Tropsch), U.S. Pat. No. 6,300,535 (MFI-bound zeolites), and mesoporous molecular sieves (U.S. Pat. Nos. 6,284,696, 5,098,684, 5,102,643 and 5,108,725), which are all herein fully incorporated by reference. Binder may no longer be necessary in such systems.

In a further embodiment, the molecular sieve of the present invention may be combined with a metal catalyst, for example as a Fischer-Tropsch catalyst.

Process for Using the Molecular Sieve Catalyst Compositions

The molecular sieve catalysts and compositions of the present invention are useful in a variety of processes including: cracking, hydrocracking, isomerization, polymerisation, reforming, hydrogenation, dehydrogenation, dewaxing, hydrodewaxing, absorption, alkylation, transalkylation, dealkylation, hydrodecylizationi, disproportionation, oligomerization, dehydrocyclization and combinations thereof.

The preferred processes of the present invention include a process directed to the conversion of a feedstock comprising one or more oxygenates to one or more olefin(s) and a process directed to the conversion of ammonia and one or more oxygenates to alkyl amines and in particular methylamines.

In a preferred embodiment of the process of the invention, the feedstock contains one or more oxygenates, more specifically, one or more organic compound(s) containing at least one oxygen atom. In the most preferred embodiment of the process of invention, the oxygenate in the feedstock is one or more alcohol(s), preferably aliphatic alcohol(s) where the aliphatic moiety of the alcohol(s) has from 1 to 20 carbon atoms, preferably from 1 to 10 carbon atoms, and most preferably from 1 to 4 carbon atoms. The alcohols useful as feedstock in the process of the invention include lower straight and branched chain aliphatic alcohols and their unsaturated counterparts.

Non-limiting examples of oxygenates include methanol, ethanol, n-propanol, isopropanol, methyl ethyl ether, dimethyl ether, diethyl ether, di-isopropyl ether, formaldehyde, dimethyl carbonate, dimethyl ketone, acetic acid, and mixtures thereof. In the most preferred embodiment, the feedstock is selected from one or more of methanol, ethanol, dimethyl ether, diethyl ether or a combination thereof, more preferably methanol and dimethyl ether, and most preferably methanol.

In the most preferred embodiment, the feedstock, preferably of one or more oxygenates, is converted in the presence of a molecular sieve catalyst composition into olefin(s) having 2 to 6 carbons atoms, preferably 2 to 4 carbon atoms. Most preferably, the olefin(s), alone or combination, are converted from a feedstock containing an oxygenate, preferably an alcohol, most preferably methanol, to the preferred olefin(s) ethylene and/or propylene.

The most preferred process is generally referred to as gas-to-olefins (GTO) or alternatively, methanol-to-olefins (MTO). In a MTO process, typically an oxygenated feedstock, most preferably a methanol containing feedstock, is converted in the presence of a molecular sieve catalyst composition into one or more olefin(s), preferably and predominantly, ethylene and/or propylene, often referred to as light olefin(s).

In one embodiment of the process for conversion of a feedstock, preferably a feedstock containing one or more oxygenates, the amount of olefin(s) produced based on the total weight of hydrocarbon produced is greater than 50 weight percent, preferably greater than 60 weight percent, more preferably greater than 70 weight percent.

The feedstock, in one embodiment, contains one or more diluent(s), typically used to reduce the concentration of the feedstock, and are generally non-reactive to the feedstock or molecular sieve catalyst composition. Non-limiting examples of diluents include helium, argon, nitrogen, carbon monoxide, carbon dioxide, water, essentially non-reactive paraffins (especially alkanes such as methane, ethane, and propane), essentially non-reactive aromatic compounds, and mixtures thereof. The most preferred diluents are water and nitrogen, with water being particularly preferred.

The diluent, water, is used either in a liquid or a vapour form, or a combination thereof. The diluent is either added directly to a feedstock entering into a reactor or added directly into a reactor, or added with a molecular sieve catalyst composition. In one embodiment, the amount of diluent in the feedstock is in the range of from about 1 to about 99 mole percent based on the total number of moles of the feedstock and diluent, preferably from about 1 to 80 mole percent, more preferably from about 5 to about 50, most preferably from about 5 to about 25. In one embodiment, other hydrocarbons are added to a feedstock either directly or indirectly, and include olefin(s), paraffin(s), aromatic(s) (see for example U.S. Pat. No. 4,677,242, addition of aromatics) or mixtures thereof, preferably propylene, butylene, pentylene, and other hydrocarbons having 4 or more carbon atoms, or mixtures thereof.

The process for converting a feedstock, especially a feedstock containing one or more oxygenates, in the presence of a molecular sieve catalyst composition of the invention, is carried out in a reaction process in a reactor, where the process is a fixed bed process, a fluidised bed process (includes a turbulent bed process), preferably a continuous fluidised bed process, and most preferably a continuous high velocity fluidised bed process.

The reaction processes can take place in a variety of catalytic reactors such as hybrid reactors that have a dense bed or fixed bed reaction zones and/or fast fluidised bed reaction zones coupled together, circulating fluidised bed reactors, riser reactors, and the like. Suitable conventional reactor types are described in for example U.S. Pat. No. 4,076,796, U.S. Pat. No. 6,287,522 (dual riser), and *Fluidization Engineering*, D. Kunii and O. Levenspiel, Robert E. Krieger Publishing Company, New York, N.Y. 1977, which are all herein fully incorporated by reference.

The preferred reactor type are riser reactors generally described in *Riser Reactor, Fluidization and Fluid-Particle Systems*, pages 48 to 59, F. A. Zenz and D. F. Othmo, Reinhold Publishing Corporation, New York, 1960, and U.S. Pat. No. 6,166,282 (fast-fluidised bed reactor), and U.S. patent application Ser. No. 09/564,613 filed May 4, 2000 (multiple riser reactor), which are all herein fully incorporated by reference.

In the preferred embodiment, a fluidised bed process or high velocity fluidised bed process includes a reactor system, a regeneration system and a recovery system.

The reactor system preferably is a fluid bed reactor system having a first reaction zone within one or more riser reactor (s) and a second reaction zone within at least one disengaging vessel, preferably comprising one or more cyclones. In one embodiment, the one or more riser reactor(s) and disengaging vessel is contained within a single reactor vessel. Fresh feedstock, preferably containing one or more oxygenates, optionally with one or more diluent(s), is fed to the one or more riser reactor(s) in which a molecular sieve catalyst composition or coked version thereof is introduced. In one embodiment, the molecular sieve catalyst composition or coked version thereof is contacted with a liquid or gas, or combination thereof, prior to being introduced to the riser reactor(s), preferably the liquid is water or methanol, and the gas is an inert gas such as nitrogen.

In an embodiment, the amount of fresh feedstock fed separately or jointly with a vapour feedstock, to a reactor system is in the range of from 0.1 weight percent to about 85 weight percent, preferably from about 1 weight percent to about 75 weight percent, more preferably from about 5 weight percent to about 65 weight percent based on the total weight of the feedstock including any diluent contained therein. The liquid and vapour feedstocks are preferably the same composition, or contain varying proportions of the same or different feedstock with the same or different diluent.

The feedstock entering the reactor system is preferably converted, partially or fully, in the first reactor zone into a gaseous effluent that enters the disengaging vessel along with a coked molecular sieve catalyst composition. In the preferred embodiment, cyclone(s) within the disengaging vessel are designed to separate the molecular sieve catalyst composition, preferably a coked molecular sieve catalyst composition, from the gaseous effluent containing one or more olefin(s) within the disengaging zone. Cyclones are preferred, however, gravity effects within the disengaging vessel will also separate the catalyst compositions from the gaseous effluent. Other methods for separating the catalyst compositions from the gaseous effluent include the use of plates, caps, elbows, and the like.

In one embodiment of the disengaging system, the disengaging system includes a disengaging vessel; typically a lower portion of the disengaging vessel is a stripping zone. In the stripping zone the coked molecular sieve catalyst composition is contacted with a gas, preferably one or a combination of steam, methane, carbon dioxide, carbon monoxide, hydrogen, or an inert gas such as argon, preferably steam, to recover adsorbed hydrocarbons from the coked molecular sieve catalyst composition that is then introduced to the regeneration system. In another embodiment, the stripping zone is in a separate vessel from the disengaging vessel and the gas is passed at a gas hourly superficial velocity (GHSV) of from 1 $hr^{-1}$ to about 20,000 $hr^{-1}$ based on the volume of gas to volume of coked molecular sieve catalyst composition, preferably at an elevated temperature from 250° C. to about 750° C., preferably from about 350° C. to 650° C., over the coked molecular sieve catalyst composition.

The conversion temperature employed in the conversion process, specifically within the reactor system, is in the range of from about 200° C. to about 1000° C., preferably from about 250° C. to about 800° C., more preferably from about 250° C. to about 750° C., yet more preferably from about 300° C. to about 650° C., yet even more preferably from about 350° C. to about 600° C. most preferably from about 350° C. to about 550° C.

The conversion pressure employed in the conversion process, specifically within the reactor system, varies over a wide range including autogenous pressure. The conversion pressure is based on the partial pressure of the feedstock exclusive of any diluent therein. Typically the conversion pressure employed in the process is in the range of from about 0.1 kPaa to about 5 MPaa, preferably from about 5 kpaa to about 1 MPaa, and most preferably from about 20 kPaa to about 500 kPaa.

The weight hourly space velocity (WHSV), particularly in a process for converting a feedstock containing one or more oxygenates in the presence of a molecular sieve catalyst composition within a reaction zone, is defined as the total weight of the feedstock excluding any diluents to the reaction zone per hour per weight of molecular sieve in the molecular sieve catalyst composition in the reaction zone. The WHSV is maintained at a level sufficient to keep the catalyst composition in a fluidised state within a reactor.

Typically, the WHSV ranges from about 1 $hr^{-1}$ to about 5000 $hr^{-1}$, preferably from about 2 $hr^{-1}$ to about 3000 $hr^{-1}$, more preferably from about 5 $hr^{-1}$ to about 1500 $hr^{-1}$, and most preferably from about 10 $hr^{-1}$ to about 1000 $hr^{-1}$. In one preferred embodiment, the WHSV is greater than 20 $hr^{-1}$; preferably the WHSV for conversion of a feedstock containing methanol and dimethyl ether is in the range of from about 20 $hr^{-1}$ to about 300 $hr^{-1}$.

The superficial gas velocity (SGV) of the feedstock including diluent and reaction products within the reactor system is preferably sufficient to fluidise the molecular sieve catalyst composition within a reaction zone in the reactor. The SGV in the process, particularly within the reactor system, more particularly within the riser reactor(s), is at least 0.1 meter per second (m/sec), preferably greater than 0.5 m/sec, more preferably greater than 1 m/sec, even more preferably greater than 2 m/sec, yet even more preferably greater than 3 m/sec, and most preferably greater than 4 m/sec. See for example U.S. patent application Ser. No. 09/708,753 filed Nov. 8, 2000, which is herein incorporated by reference.

In one preferred embodiment of the process for converting an oxygenate to olefin(s) using a silicoaluminophosphate molecular sieve catalyst composition, the process is operated at a WHSV of at least 20 $hr^{-1}$ and a Temperature Corrected Normalized Methane Selectivity (TCNMS) of less than 0.016, preferably less than or equal to 0.01. See for example U.S. Pat. No. 5,952,538, which is herein fully incorporated by reference.

In another embodiment of the processes for converting an oxygenate such as methanol to one or more olefin(s) using a molecular sieve catalyst composition, the WHSV is from 0.01 $hr^{-1}$ to about 100 $hr^{-1}$, at a temperature of from about 350° C. to 550° C., and silica to $Me_2O_3$ (Me is a Group IIIA or VIII element from the Periodic Table of Elements) molar ratio of from 300 to 2500. See for example EP-0 642 485 B1, which is herein fully incorporated by reference.

Other processes for converting an oxygenate such as methanol to one or more olefin(s) using a molecular sieve catalyst composition are described in PCT WO 01/23500 published Apr. 5, 2001 (propane reduction at an average catalyst feedstock exposure of at least 1.0), which is herein incorporated by reference.

The coked molecular sieve catalyst composition is withdrawn from the disengaging vessel, preferably by one or more cyclones(s), and introduced to the regeneration system. The regeneration system comprises a regenerator where the coked catalyst composition is contacted with a regeneration medium, preferably a gas containing oxygen, under general regeneration conditions of temperature, pressure and residence time.

Non-limiting examples of the regeneration medium include one or more of oxygen, $O_3$, $SO_3$, $N_2O$, NO, $NO_2$, $N_2O_5$, air, air diluted with nitrogen or carbon dioxide, oxygen and water (U.S. Pat. No. 6,245,703), carbon monoxide and/or hydrogen. The regeneration conditions are those capable of burning coke from the coked catalyst composition, preferably to a level less than 0.5 weight percent based on the total weight of the coked molecular sieve catalyst composition entering the regeneration system. The coked molecular sieve catalyst composition withdrawn from the regenerator forms a regenerated molecular sieve catalyst composition.

The regeneration temperature is in the range of from about 200° C. to about 1500° C., preferably from about 300° C. to about 1000° C., more preferably from about 450° C. to about 750° C., and most preferably from about 550° C. to 700° C. The regeneration pressure is in the range of from about 15 psia (103 kpaa) to about 500 psia (3448 kpaa), preferably from about 20 psia (138 kPaa) to about 250 psia (1724 kPaa), more preferably from about 25 psia (l72kPaa) to about 150 psia (1034 kPaa), and most preferably from about 30 psia (207 kpaa) to about 60 psia (414 kPaa).

The preferred residence time of the molecular sieve catalyst composition in the regenerator is in the range of from about one minute to several hours, most preferably about one minute to 100 minutes, and the preferred volume of oxygen in the gas is in the range of from about 0.01 mole percent to about 5 mole percent based on the total volume of the gas.

In one embodiment, regeneration promoters, typically metal containing compounds such as platinum, palladium and the like, are added to the regenerator directly, or indirectly, for example with the coked catalyst composition. Also, in another embodiment, a fresh molecular sieve catalyst composition is added to the regenerator containing a regeneration medium of oxygen and water as described in U.S. Pat. No. 6,245,703, which is herein fully incorporated by reference.

In an embodiment, a portion of the coked molecular sieve catalyst composition from the regenerator is returned directly to the one or more riser reactor(s), or indirectly, by pre-contacting with the feedstock, or contacting with fresh molecular sieve catalyst composition, or contacting with a regenerated molecular sieve catalyst composition or a cooled regenerated molecular sieve catalyst composition described below.

The burning of coke is an exothermic reaction, and in an embodiment, the temperature within the regeneration system is controlled by various techniques in the art including feeding a cooled gas to the regenerator vessel, operated either in a batch, continuous, or semi-continuous mode, or a combination thereof. A preferred technique involves withdrawing the regenerated molecular sieve catalyst composition from the regeneration system and passing the regenerated molecular sieve catalyst composition through a catalyst cooler that forms a cooled regenerated molecular sieve catalyst composition. The catalyst cooler, in an embodiment, is a heat exchanger that is located either internal or external to the regeneration system.

In one embodiment, the cooler regenerated molecular sieve catalyst composition is returned to the regenerator in a continuous cycle, alternatively, (see U.S. patent application Ser. No. 09/587,766 filed Jun. 6, 2000) a portion of the cooled regenerated molecular sieve catalyst composition is returned to the regenerator vessel in a continuous cycle, and another portion of the cooled molecular sieve regenerated molecular sieve catalyst composition is returned to the riser reactor(s), directly or indirectly, or a portion of the regenerated molecular sieve catalyst composition or cooled regenerated molecular sieve catalyst composition is contacted with by-products within the gaseous effluent (PCT WO 00/49106 published Aug. 24, 2000), which are all herein fully incorporated by reference. In another embodiment, a regenerated molecular sieve catalyst composition contacted with an alcohol, preferably ethanol, 1-propnaol, 1-butanol or mixture thereof, is introduced to the reactor system, as described in U.S. patent application Ser. No. 09/785,122 filed Feb. 16, 2001, which is herein fully incorporated by reference.

Other methods for operating a regeneration system are in disclosed U.S. Pat. No. 6,290,916 (controlling moisture), which is herein fully incorporated by reference.

The regenerated molecular sieve catalyst composition withdrawn from the regeneration system, preferably from the catalyst cooler, is combined with a fresh molecular sieve catalyst composition and/or re-circulated molecular sieve catalyst composition and/or feedstock and/or fresh gas or liquids, and returned to the riser reactor(s). In another embodiment, the regenerated molecular sieve catalyst composition withdrawn from the regeneration system is returned to the riser reactor(s) directly, preferably after passing through a catalyst cooler. In one embodiment, a carrier, such as an inert gas, feedstock vapour, steam or the like, semi-continuously or continuously, facilitates the introduction of the regenerated molecular sieve catalyst composition to the reactor system, preferably to the one or more riser reactor(s).

By controlling the flow of the regenerated molecular sieve catalyst composition or cooled regenerated molecular sieve catalyst composition from the regeneration system to the reactor system, the optimum level of coke on the molecular sieve catalyst composition entering the reactor is maintained. There are many techniques for controlling the flow of a molecular sieve catalyst composition described in Michael Louge, *Experimental Techniques, Circulating Fluidised Beds*, Grace, Avidan and Knowlton, eds. Blackie, 1997 (336–337), which is herein incorporated by reference.

Coke levels on the molecular sieve catalyst composition are measured by withdrawing from the conversion process the molecular sieve catalyst composition at a point in the process and determining its carbon content. Typical levels of coke on the molecular sieve catalyst composition, after regeneration is in the range of from 0.01 weight percent to about 15 weight percent, preferably from about 0.1 weight percent to about 10 weight percent, more preferably from about 0.2 weight percent to about 5 weight percent, and most preferably from about 0.3 weight percent to about 2 weight percent based on the total weight of the molecular sieve and not the total weight of the molecular sieve catalyst composition.

In one preferred embodiment, the mixture of fresh molecular sieve catalyst composition and regenerated molecular sieve catalyst composition and/or cooled regenerated molecular sieve catalyst composition contains in the range of from about 1 to 50 weight percent, preferably from about 2 to 30 weight percent, more preferably from about 2 to about 20 weight percent, and most preferably from about 2 to about 10 coke or carbonaceous deposit based on the total weight of the mixture of molecular sieve catalyst compositions. See for example U.S. Pat. No. 6,023,005, which is herein fully incorporated by reference.

The gaseous effluent is withdrawn from the disengaging system and is passed through a recovery system. There are many well-known recovery systems, techniques and sequences that are useful in separating olefin(s) and purifying olefin(s) from the gaseous effluent. Recovery systems generally comprise one or more or a combination of a various separation, fractionation and/or distillation towers, columns, splitters, or trains, reaction systems such as ethylbenzene manufacture (U.S. Pat. No. 5,476,978) and other derivative processes such as aldehydes, ketones and ester manufacture (U.S. Pat. No. 5,675,041), and other associated equipment for example various condensers, heat exchangers, refrigeration systems or chill trains, compressors, knock-out drums or pots, pumps, and the like.

The molecular sieves of the present invention and catalyst compositions of the present invention may be used in the manufacture of alkylamines, using ammonia. Examples of suitable processes are as described in published European Patent Application EP 0 993 867 A1, and in U.S. Pat. No. 6,153,798 to Hidaka et.al, which are herein fully incorporated by reference.

In order to provide a better understanding of the present invention including representative advantages thereof, the following examples are offered.

EXAMPLES

XRD

X-ray Powder Diffractograms were recorded on a Siemens D500 diffractometer with voltage of 40 kV and current of 30 mA, using a Cu target and Ni-filter ($\lambda$=0.154 nm). Elemental analysis of Al, Si, and P was performed using the Inductively Coupled Plasma (ICP) spectroscopy.

Methanol Conversion

In these examples, the catalytic performances of some of the low silica silicoaluminophosphate molecular sieves prepared in the following Examples was tested. The conversion of methanol to light olefins, and, in particular, the selectivity for ethylene and propylene was evaluated for these catalysts.

Conversion reactions in which methanol (MeOH) was converted to olefin product were carried out in a fixed bed reactor with continuous flow of MeOH vapor (WHSV=100 hr$_1$) with no diluent at 475° C. The pressure within the reactor was maintained at 25 psig (274 kPa or 2.70 atm).

Prior to being loaded into the reactor the molecular sieves were calcined in air at 650° C. for three hours and the calcined powders were pressed into tablets. The prepared tablets were then crushed to pellets with 20–40 mesh size. The catalysts were activated at 500° C. in flowing N$_2$ for one hour prior to initiating the MeOH feed. The reaction products were analyzed using an on-line gas chromatograph equipped with a boiling point column and a FID detector. The test results summarize the average performance of the molecular sieve of the invention over the entire on-stream lifetime of the catalysts

Comparative Example 1

Preparation of Silicoaluminophosphates of the CHA Framework Type Using N,N-dimethylethanolamine (DMEA) as Template The following ingredients were mixed, in sequence, and blended into a uniform gel using a microhomogenizer (Tissue Tearor Model 98730 available from Biospec Products, Inc, USA): 85 wt % H$_3$PO$_4$ (obtained from Aldrich Chemical Company), H$_2$O, Cabosil™ (fumed silica available from Cabot Corporation, Ill., USA), Catapal™ A (71.5 wt % Al$_2$O$_3$, available from CONDEA Vista Company, Texas, USA), and then N, N-dimethylethanolamine (DMEA) (obtained from Aldrich Chemical Company, USA). The molar ratio of the ingredients was as follows:

3.0 DMEA: 1.0 Al$_2$O$_3$:0.3 SiO$_2$:1.0 P$_2$O$_5$:50 H$_2$O

The gel was then placed into a Parr bomb with Teflon liner, and was heated to 180° C. for 10 days. The solid product was centrifuged and washed several times with deionized water, and was then dried in a 60° C. vacuum oven overnight to provide a silicoaluminophosphate of the CHA framework type, comprising N,N-dimethylethanolamine within its intra-crystalline structure. X-ray powder patterns of the product confirmed that the product is a silicoaluminophosphate of the CHA framework type. The solid product yield was 7.70% after 10 days of crystallization, based on the weight of the starting synthesis mixture. Elemental analysis of the products gives the following molar composition Al$_{1.0}$Si$_{0.209}$P$_{0.799}$. The final product has a Si/Al ratio of 0.209, which equates to a number of Si/Cage of 1.25

This example shows that relatively pure silicoaluminophosphates of the CHA framework type may be synthesized with N,N-dimethylethanolarnine as template. Typically when TEAOH is used as the template in such a synthesis the Si/Al ratio is 0.167. The Si/Al atomic ratio of the N,N-dimethylethanolamine derived product is determined at 0.209 by elemental analysis. This indicates that the Si/CHA cage ratio is greater than 1 when N,N-dimethylethanolamine is used on its own as template.

Comparative Example 2

Preparation of Low Silica SAPO Having the CHA Framework Type Using DMEA as Template and HF 8.36 g H$_3$PO$_4$ (85%), 25.01 g H$_2$O, 4.35 g Catapal™, 0.21 g Cabosil™, and 7.06 g N, N-dimethylethanolamine were mixed, in sequence, into a uniform gel with a microhomogenizer. To the mixture was added 0.70 g HF (50%), and the mixture was stirred at room temperature overnight. The composition of the gel was as follows:

2.5 DMEA:0.5HF:1.0Al$_2$O$_3$:0.1SiO$_2$:1.15P$_2$O$_5$:50H$_2$O

The mixture was divided into equal parts, which were then sealed in a Teflon lined Parr bomb before $_{being}$ heated to 180° C. for 2 and 5 days. The solid product was centrifuged and washed several times with deionized water, and was dried in a 60° C. vacuum oven. The X-ray powder diffraction patterns indicated that these products have X-ray powder diffraction patterns that differ from those of typical pre-calcined silicoaluminophosphates of CHA framework type. The product yields were 7.7%, and 15.2% after 2 and 5 days of crystallization, respectively, based on the weight of the starting gel.

Elemental $_{analysis}$ of the product obtained after 2 days of crystallization gave the following results: Al, 17.0%; Si, 0.924%; P, 17.8%, F, 2.86%; which corresponds to the following composition: F$_{0.239}$Al$_{1.0}$Si$_{0.052}$P$_{0.912}$. The silicoaluminophosphate had a Si/Al ratio of 0.052 and a Si/CHA cage ratio of 0.052/0.167=0.31. This example shows that DMEA can be mixed with HF to produce a SAPO material having a low Si content.

Figure 2:
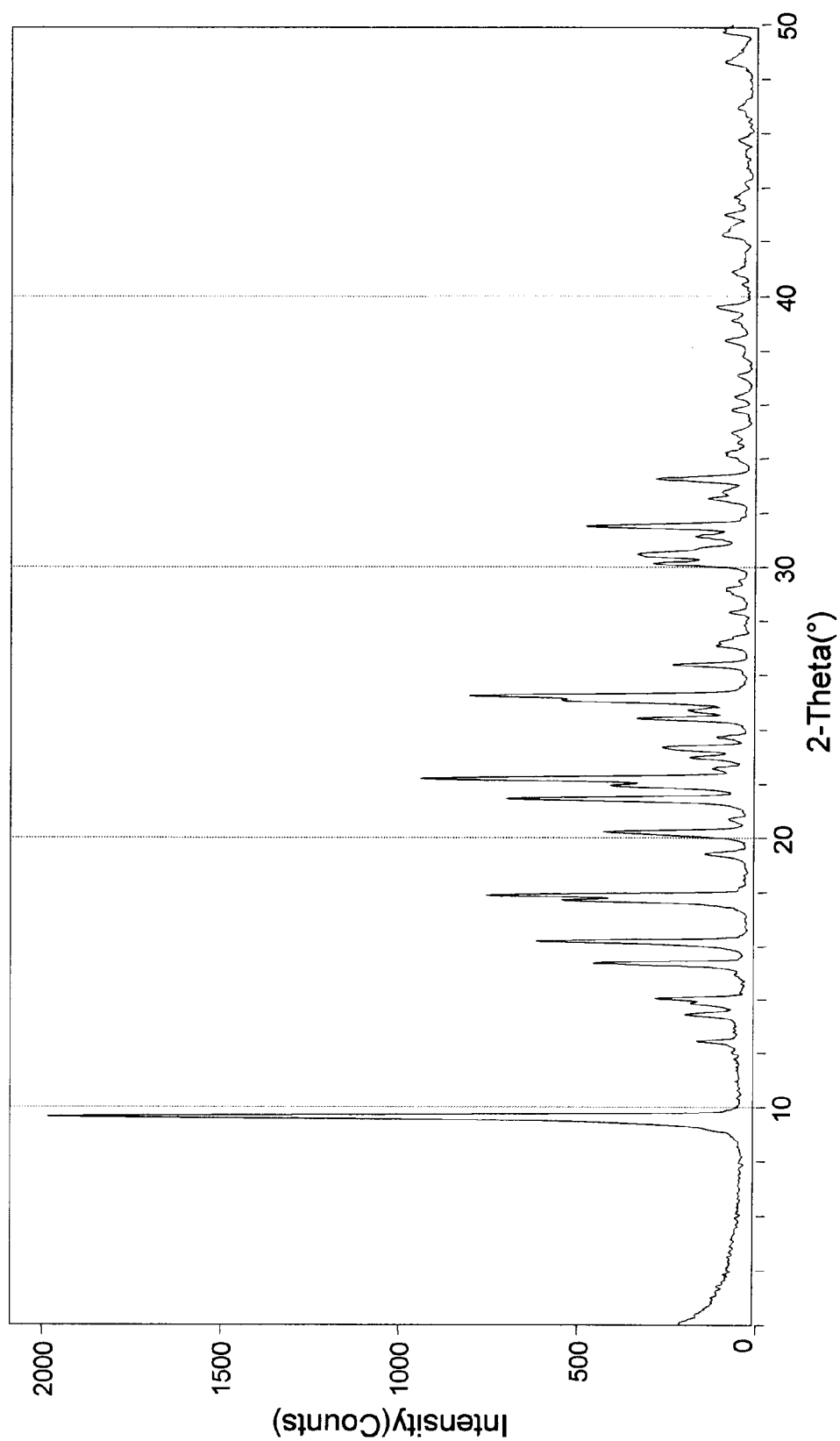
FIG. 2 shows a typical X-ray powder diffraction pattern of a SAPO of CHA framework type according to the present invention.

The material obtained after 5 days of crystallization, is calcined at 550° C. for two hours then at 600° C. $_{for}$ one hour to remove the template and the fluoride ion. The white powder is immediately analyzed after calcination, but with no precaution to avoid exposure to moisture, using X-ray powder diffraction. This confirms that the low silica materials obtained with N,N-dimethylethanolamine template and HF, have a CHA framework type after calcination. The uncalcined materials exhibit a unique XRD pattern from which it is not apparent that the framework has the CHA framework (see FIG. 2).

Example 1

Preparation of Low Silica SAPO Having the CHA Framework Type Using DMEA and Ammonium Hexafluorosilicate (AHFS)

The following ingredients are mixed, in sequence, and blended into a uniform gel using a microhomogenizer:

$H_3PO_4$, $H_2O$, Catapal™, Cabosil™, N,N-dimethylethanolamine (DMEA), and lastly $(NH_4)_2SiF_6$ (AHFS). The molar ratio of the ingredients was as follows:

2.0DMEA:1.0$Al_2O_3$:0.05$SiO_2$:1.15$P_2O_5$: 25$H_2O$:0.0375 $(NH_4)_2SiF_6$

To make 200 g of gel, for example, 57.07 g 85% phosphoric acid are added to 74.14 g deionized water. Then 29.70 g Catapal™ ($Al_2O_3 2H_2O$) is added with vigorous stirring. To the resulting gel is added 0.72 g Cabosil™ (fumed silica), 38.37 g N,N-dimethylethanolamine, and 1.60 g ammonium hexafluorosilicate. The mixture is blended into a uniform gel and was then allowed to age at room temperature for 18 hours. The gel is then transferred into a 300 cc stirred autoclave and is then sealed and heated to 170° C. over 18 hours, and is held at the temperature for 18 hours. The solid product is centrifuged and washed four times with deionized water, and is then dried in a 60° C. vacuum oven overnight. The solid yield based on the weight of the gel is 27.3 wt %. X-ray powder diffraction pattern of the product is compared with the XRD pattern of the product obtained with DMEA and HF in Comparative Example 2. This comparison indicates that the products are nearly identical. Elemental analysis of the products gives the following molar composition: $Al_{1.0}Si_{0.058}P_{0.940}$ for the product. The Si/Al ratio is 0.058, which indicates a Si/CHA cage of 0.35. This example shows that ammonium hexafluorosilicate can be an effective alternative fluoride source to hydrofluoric acid (HF), to afford low silica SAPO of CHA framework type in high yield.

Example 2

Preparation of Low Silica SAPO Having CHA Framework Type Using DMEA and Ammonium Hexafluorosilicate (AHFS)

The ingredient source and procedure is identical to that used in Example 1, except that no Cabosil™ is added. AHFS is the source of both fluoride and silica. The molar ratio of ingredients is the following:

2.0DMEA:1.0$Al_2O_3$:0.1$(NH_4)_2SiF_6$:1.15$P_2O_5$:30$H_2O$

The gel is divided into several aliquots, which are sealed and heated without stirring in a 170° C. oven. The products are washed with deionized water and dried at 60° C. XRD analysis indicates that after four days of crystallization the product has the typical pattern of low Si SAPO34 plus minor amount (less than 5 wt %) of $AlPO_4$-15 impurity (peak at between 10 and 12°2θ, ICDD database card# 40-0404). $AlPO_4$-15 is an aluminohydroxyphosphate with ammonium cations and is a relatively inert impurity. The yield is 17.9 wt % based on the gel weight. The product composition is $Al_{1.0}Si_{0.047}P_{0.966}$. The ratio of Si/Al is 0.047, which indicates an Si/CHA cage of 0.28 This example illustrates that low Si SAPO of CHA framework type can be obtained using ammonium hexafluorosilicate as both the fluoride source and the silica source and without the use of HF.

Since the XRD pattern of this low Si SAPO material cannot be fitted to any known powder pattern, it is necessary to confirm that the framework topology of the product has the chabazite (CHA) framework type.

The product was calcined at 600° C. for two hours to remove both fluoride incorporated in the structure and the organic template. The freshly calcined sample was then soaked in methanol, and the moist sample is placed in a 200° C. oven to dry. This dry sample was quickly placed on an X-ray diffractometer and the XRD pattern was taken with minimal exposure to moisture in air. The XRD pattern confirms that the calcined material has the CHA framework type (ICDD database card #34-0137).

Example 3

Low Silica SAPO Having CHA Framework Type Using Ammonium Hexafluorophosphate ($NH_4PF_6$, AHFP) as fluoride source.

The ingredient source and procedure is identical to that used in Example 1, except that ammonium hexafluorophosphate (AHFP) is the source of fluoride. The molar ratio of ingredients was the following:

2.0DMEA:1.0$Al_2O_3$:0.1$SiO_2$:1.15$P_2O_5$: 25$H_2O$:0.1$NH_4PF_6$

The gel was divided into several aliquots, which were sealed and heated without stirring in a 170° C. oven. The products were washed with deionized water and dried at 60° C. XRD indicates that after 1 day of crystallization the product has the typical pattern of pure low Si SAPO of CHA framework type. It is also observed that the product crystallinity deteriorated with increased crystallization periods of up to 6 days. The yield was 10.9 and 16.7 wt % after 1 and 4 days of crystallization, based on the gel weight. The product composition was $Al_{1.0}Si_{0.155}P_{0.955}$ and $Al_{1.0}Si_{0.073}P_{0.975}$ for products after one and four days of crystallization, respectively. The Si/Al ratios were 0.155 and 0.073, respectively, indicating Si/CHA cage ratios of 0.93 and 0.44, respectively.

Example 4

Low Silica SAPO Having the CHA Framework Type Using Tetraethylammonium Hexafluorophosphate, $TEAPF_6$ The ingredient source and procedure is identical to that used in Example 1, except that $[(C_2H_5)_4N]PF_6$ (referred to as $TEAPF_6$), is the source of fluoride. The molar ratio of ingredients was the following:

2.0DMEA: 1.0$Al_2O_3$:0.1$SiO_2$:1.15$P_2O_5$: 25$H_2O$:0.1 $[(C_2H_5)_4N]PF_6$

The gel was sealed and heated without stirring in a 170° C. oven. The product was washed with deionized water and dried at 60° C. XRD indicates that after 1 day of crystallization the product has the typical pattern of pure F-containing low Si SAPO of CHA framework type. In addition, the product crystallinity did not deteriorate with extended periods of up to 6 days of crystallization. The yield was 17.2 wt % after one day of crystallization, based on the gel weight. The product composition was $Al_{1.0}Si_{0.063}P_{0.968}$. The Si/Al ratio of the product was 0.063, which indicates a Si/CHA cage of 0.38. This example illustrates that when $[(C_2H_5)_4N]PF_6$ is used as the source of fluoride a more stable crystalline product is obtained compared to that obtained when $NH_4PF_6$ is used as the source of fluoride.

The products obtained after 1 day of crystallization in Examples 3 and 4, were calcined at 550° C. for two hours then at 600° C. for one hour to remove the template and the fluoride ion. The white powder was immediately analyzed using X-ray Powder Diffraction, indicating that the calcined materials have the CHA framework type.

Example 5

Preparation of Low Silica SAPO Having the CHA Framework Type Using Morpholine and Ammonium Hexafluorophosphate (AHFP)

The ingredient source and procedure are identical to Example 1, except that the template is morpholine instead of DMEA, and AHFP is the source of fluoride. The molar ratios of the ingredients were as follows:

2.0 Morpholine:1.0$Al_2O_3$:0.1$SiO_2$:0.1$NH_4PF_6$:1.15$P_2O_5$: 25$H_2O$

The gel was sealed and heated without stirring in a 170° C. oven. The product was washed with deionized water and dried at 60° C. XRD indicates that after one day of crystallization the product has the typical pattern of fluoride-containing low Si SAPO of CHA framework type. Minor amounts of $AlPO_4$-15 impurity (peak at between 10 and 12°2θ ICDD database card# 40-0404) were formed in the product. The yield was 17.4 wt % after one day of crystallization based on the gel weight. The product composition was $Al_{1.0}Si_{0.027}P_{0.999}$. The Si/Al ratio of the product was 0.027, giving Si/CHA cage ratios of 0.16. This example shows that low Si SAPO material having the CHA framework type can be synthesized with fluoride sources other than HF and organic templates other than DMEA.

rophosphoric acid as a fluoride source and DMEA as template. The advantage of this fluoride source over AHFP or AHFS is that it introduces no ammonium ion, which may be causing $AlPO_4$-15 impurity. Hexafluorosilicic acid, $H_2SiF_6$, also commercially available, offers a similar advantage.

Example 7

Synthesis of SAPO's of the CHA Framework Type with $HPF_6$—MTO Performance

Two samples were prepared using the general procedure of Example 1. The molar ratios of synthesis mixture and results of the synthesis are provided in Table 1.

TABLE 1

| F Cmpd | Morpholine | DMEA | $P_2O_5$ | $Al_2O_3$ | $SiO_2$ | $H_2O$ | Temp ° C. | Time hours | Yield wt % | Si/Al Product | Si/CHA cage |
|---|---|---|---|---|---|---|---|---|---|---|---|
| 0.1 $HPF_6$ | 0 | 1.5 | 1 | 1 | 0.1 | 34 | 170 | 20 | 26.5 | 0.059 | 0.35 |
| 0.05 $HPF_6$ | 0.5 | 1.0 | 1 | 1 | 0.1 | 34 | 150 | 20 | 19.7 | 0.040 | 0.24 |

Example 6
Preparation of Low Silica SAPO of the CHA Framework Type DMEA and Hexafluorophosphoric Acid (HFPA)

The ingredient source and procedure are identical to Example 1, except that the fluoride source is hexafluoro phosphoric acid (Aldrich, $HPF_6$, 70%; 60% as HPF6). The molar ratio of ingredients was the following:

2.0 DMEA:1.0$Al_2O_3$:0.1$SiO_2$:0.1$HPF_6$:1.15$P_2O_5$:34$H_2O$

The gel was sealed in a 300 ml autoclave and heated with stirring (240 rpm) at 20° C./min to 170° C., then held at that temperature for 20 hours. The product was washed with deionized water four times and dried at 60° C. in a vacuum oven. XRD indicated that the product has the typical pattern of fluoride-containing, low Si SAPO of CHA framework type, free of $AlPO_4$-15 impurity. The yield was 22.0 wt % based on the gel weight. The product composition was $Al_{1.0}Si_{0.034}P_{0.992}$. The Si/Al ratio of 0.034 is indicative of an Si/CHA cage of 0.20.

This example shows that low Si SAPO material of the CHA framework type can be synthesized with the hexafluo One of the preparations presented in the Table employs both morpholine and DMEA as templates. These two samples were evaluated for MTO conversion performance as described above and the results are provided in Table 2.

TABLE 2

| $C_2$= + $C_3$= | $C_4$+ | $CH_4$ | $C_2$= | $C_2°$ | $C_3$= | $C_3°$ | 1-$C_4°$ | 1-$C_4$= | 2-$C_4$= |
|---|---|---|---|---|---|---|---|---|---|
| 76.82 | 17.19 | 2.16 | 35.40 | 0.41 | 41.43 | 0.68 | 0.08 | 4.47 | 9.56 |
| 76.06 | 17.24 | 2.22 | 35.59 | 0.47 | 40.48 | 1.02 | 0.13 | 4.68 | 9.74 |

The table shows weight selectivity data for MTO reactions carried out at 475° C., WHSV=100/h, with no diluent. The selectivity data shown is the average of more than five data points taken with equal intervals while the catalysts maintained greater than 50% oxygenate (methanol and dimethylether) conversion. The initial conversion under these reaction conditions is typically greater than 90% and the conversion generally declines with time.

The combination of $HPF_6$ and DMEA provides a material that gives combined ethylene and propylene selectivity of about 76%. In addition the combination of DMEA and morpholine with $HPF_6$ also produces very good results.

Example 8

Synthesis of SAPO of CHA Framework Type with Variations in Amount of $HPF_6$

Three samples were prepared using the general procedure of Example 7. The molar ratios of the synthesis mixture and results of the synthesis are provided in Table 3.

TABLE 3

| F Cmpd | DMEA | $P_2O_5$ | $Al_2O_3$ | $SiO_2$ | $H_2O$ | Temp °C. | Time hours | Yield wt % | Si/Al Product | Si/CHA cage | Phase Purity |
|---|---|---|---|---|---|---|---|---|---|---|---|
| 0.1 $HPF_6$ | 1.5 | 1 | 1 | 0.1 | 34 | 170 | 20 | 26.5 | 0.052 | 0.31 | Pure CHA |
| 0.05 $HPF_6$ | 1.5 | 1 | 1 | 0.1 | 34 | 150 | 20 | 10.6 | 0.063 | 0.38 | Pure CHA |
| 0.033 $HPF_6$ | 1.5 | 1 | 1 | 0.1 | 34 | 150 | 20 | 13.5 | 0.047 | 0.28 | CHA + AFI Mix |

These results show that when the $PF_6/Al_2O_3$ mole ratio is less than about 0.035 then an impure product is obtained.

Example 9

Synthesis of Low Si SAPO of CHA Framework Type with $HPF_6$ and Varying Amounts of DMEA Template.

Three samples were prepared using the general procedure of Example 7. Formulations used and results of the synthesis are provided in Table 4.

When the crystallization is undertaken with a source of fluoride other than HF and in the presence of mixed template profound effects on crystallite size and morphology are observed. Those examples which were prepared using morpholine (0.5) and DMEA (1.0) exhibit a new twinned morphology for SAPO's of CHA framework type (see FIG. 1). This twinned material exhibits very good selectivity for light olefins in the MTO reaction, vide supra Example 7.

TABLE 4

| F Cmpd | DMEA | $P_2O_5$ | $Al_2O_3$ | $SiO_2$ | $H_2O$ | Temp °C. | Time Hours | Yield wt % | Si/Al Product | Si/CHA cage | Notes |
|---|---|---|---|---|---|---|---|---|---|---|---|
| 0.1 $HPF_6$ | 2 | 1 | 1 | 0.1 | 34 | 170 | 20 | 23.8 | 0.027 | 0.16 | Pure |
| 0.1 $HPF_6$ | 2 | | | | | 150 | 20 | 25.3 | 0.052 | 0.31 | Pure |
| 0.033 $NH_4PF_6$ | 1.0 | 1 | 1 | 0.1 | 34 | 160 | 48 | 28.8 | 0.040 | 0.24 | Minor Impurity |

The products were XRD pure. However SEM revealed trace amounts of amorphous material when the molar ratio of DMEA to $Al_2O_3$ was 1.0. When the DMEA to $Al_2O_3$ molar ratio is greater than 1.0 a high yield and high purity product is obtained.

Example 10

Synthesis of Low Si SAPO of CHA Framework Type with $HPF_6$ and Varying Compositions of Mixed Templates Five samples were prepared using the general procedure of Example 7. Formulations used and results of the synthesis are provided in Table 5.

Example 11

Effect of Order of Addition of F and Si Containing Compounds

Two samples were prepared using the general procedure of Example 7, except that tetraethylorthosilicate (TEOS) was used as the silica source and fluorosilicic acid (25 wt % available from Aldrich Chemical Company, USA) was used as both fluoride source and additional silica source. The gel formulations and the results of the synthesis are provided in Table 6.

TABLE 5

| F Cmpd | Morpholine | DMEA | $P_2O_5$ | $Al_2O_3$ | $SiO_2$ | $H_2O$ | Si/Al Product | Si/CHA Cage | Morphology |
|---|---|---|---|---|---|---|---|---|---|
| 0.1 $HPF_6$ | 0 | 1.5 | 1 | 1 | 0.1 | 34 | 0.059 | 0.35 | 2 × 5μ Plates No Twinning |
| 0.1 $HPF_6$ | 0.5 | 1.0 | 1 | 1 | 0.1 | 34 | 0.042 | 0.25 | 2 × 5μ Plates Some Twinning |
| 0.1 $HPF_6$ | 1.0 | 0.5 | 1 | 1 | 0.1 | 34 | 0.032 | 0.19 | 10μ Long Prizm No Twinning |
| 0.1 $HPF_6$ | 1.5 | 0 | 1 | 1 | 0.1 | 34 | 0.024 | 0.14 | 2μ Cubes No Twinning |
| 0.05 $HPF_6$ | 0.5 | 1.0 | 1 | 1 | 0.1 | 34 | 0.040 | 0.24 | 1μ Thick Plates Heavy Twinning |

TABLE 6

| F Cmpd | DMEA | $P_2O_5$ | $Al_2O_3$ | $SiO_2$ | $H_2O$ | Temp ° C. | Time Hours | Yield wt % | Si/Al Product | Si/CHA cage |
|---|---|---|---|---|---|---|---|---|---|---|
| $0.1H_2SiF_6$ (LAST) | 1.5 | 1 | 1 | 0.1 TEOS | 34 | 170 | 20 | 25.4 | 0.085 | 0.51 |
| $0.1H_2SiF_6$ (FIRST) | 1.5 | 1 | 1 | 0.1 TEOS | 34 | 150 | 20 | 21.0 | 0.040 | 0.24 |

These result show that the order of addition when the F source is also a source of Si has an effect on the Si/Al ratio. When added last the final CHA product has twice as much Si in the resulting product. This indicates that in order to obtain low Si/CHA cage SAPO materials using $H_2SiF_6$ as the source of F and Si, $H_2SiF_6$ should preferably be added first to the reaction mixture. On the other hand, if one wishes to increase the level of silicon incorporation in the molecular sieve, $H_2SiF_6$ should preferably be added last to the reaction mixture.

Example 12

Effect of Surfactant

Two samples were prepared using the general procedure of Example 1 but with the addition of a cationic surfactant modifier. Formulations used and results of the synthesis are provided in Table 7. Tetraethylorthosilicate (TEOS) was used as silicon source in this case.

TABLE 7

| Modifier | F Cmpd | DMEA | $P_2O_5$ | $Al_2O_3$ | $SiO_2$ | $H_2O$ | Temp ° C. | Time hours | Yield wt % | Crystal Size |
|---|---|---|---|---|---|---|---|---|---|---|
| None | 0.1 $HPF_6$ | 1.5 | 1 | 1 | 0.1 | 34 | 170 | 20 | 27.3 | 3μ Prism |
| 0.01 mole | 0.1 $HPF_6$ | 1.5 | 1 | 1 | 0.1 | 34 | 170 | 20 | 25.3 | 0.3 × 0.5 × 2μ Rod |

The surfactant used was n-$C_{16}H_{33}N(CH_3)_3{}^+Cl^-$ (TMCA$^+$ Cl$^-$).

Example 13

Effect of Temperature

Two samples were prepared using the general procedure of Example 1 but different crystallization temperatures. Formulations used and results of the synthesis are provided in Table 8.

TABLE 8

| F Cmpd | DMEA | $P_2O_5$ | $Al_2O_3$ | $SiO_2$ | $H_2O$ | Temp, ° C. | Time, Hours | Yield wt % | Crystal Size |
|---|---|---|---|---|---|---|---|---|---|
| 0.1 $NH_4PF_6$ | 1.5 | 1 | 1 | 0.1 | 34 | 150 | 72 | 28.6 | 2μ Prism |
| 0.1 $NH_4PF_6$ | 1.5 | 1 | 1 | 0.1 | 34 | 160 | 48 | 25.5 | 10μ Prism |

These results show that a lower temperature gives smaller crystallites but longer crystallization times are needed.

What is claimed is:

1. A method for preparing aluminophosphate or silicoaluminophosphate molecular sieves, which process comprises;
   a. forming a reaction mixture comprising a source of aluminum, a source of phosphorus, at least one organic template, at least one compound which comprises two or more fluorine substituents and capable of providing fluoride ions, and, optionally, a source of silicon, and
   b. inducing crystallization of aluminophosphate or silicoaluminophosphate molecular sieve from the reaction mixture.

2. The method of claim 1, wherein the organic template comprises one or more of the following: tetraethyl ammonium hydroxide (TEAOH), tetraethyl ammonium phosphate, tetraethyl ammonium fluoride, tetraethyl ammonium bromide, tetraethyl ammonium chloride, tetraethyl ammonium acetate, dipropylamine (DPA), isopropylamine, cyclohexylamine, morpholine, methylbutylamine, morpholine, diethanolamine, or triethylamine.

3. The method of claim 1, wherein the organic template comprises one or more N,N-dialkylamino moieties.

4. The method of claim 3, wherein the organic template has the following general structure:

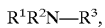

wherein $R^1$ and $R^2$ are independently selected from the group consisting of linear or branched alkyl groups having from 1 to 5 carbon atoms and $R^3$ is selected from the group consisting of linear or branched alkyl groups having from 1 to 12 carbon atoms, cycloalkyl groups having from 1 to 8 carbon atoms, linear or branched alcohols having from 1 to 12 carbon atoms, linear or branched amine-containing groups having from 1 to 12 carbon atoms.

5. The method of claim 4, wherein $R^1$ and $R^2$ are independently selected from the group consisting of methyl, ethyl, n-propyl and i-propyl, n-butyl and its branched isomers, n-pentyl and its branched isomers and $R^3$ is selected from the group consisting of methyl, ethyl, n-propyl and i-propyl, n-butyl and its branched isomers, n-pentyl and its branched isomers, n-hexyl and its branched isomers, n-heptyl and its branched isomers, and all these alkyl groups substitutes by one or several OH or $NH_2$ groups.

6. The method of claim 1, wherein the fluorine containing compound is selected from one or more of the following: $[(C_2H_5)_4N]$ PF6, $NaHF_2$, $HPF_6$, $NH_4PF_6$, $H_2SiF_6$, $(NH_4)_2SiF_6$, $NH_4HF_2$, $NaPF_6$, $AlF_3$ (anhydrous or hydrate), $(NH_4)_3AlF_6$, $(NH_4)_2TiF_6$, $(NH_4)_2ZrF_6$, $(NH_4)_2GeF_6$, $(NH_4)_2SnF_6$.

7. The method of claim 6, wherein the fluorine-containing compound is selected from one or more of the following: $(NH_4)_2SiF_6$, $NH_4HF_2$, $HPF_6$, $H_2SiF_6$, $AlF_3$ (anhydrous or hydrate), $NH_4PF_6$, $NaPF_6$.

8. The method of claim 7, wherein the fluorine-containing compound is selected from one or more of the following: $(NH_4)_2SiF_6$, $HPF_6$, $H_2SiF_6$, $AlF_3$ (anhydrous or hydrate), $NH_4PF_6$.

9. The method of claim 1, wherein the fluuorine-containing compound is $[NH_4]PF_6$ or $HPF_6$ or mixtures thereof.

10. The method of claim 1, wherein a crystal size modifier is incorporated into the reaction mixture.

11. The method of claim 10, wherein the modifier is a cationic surfactant.

12. The method of claim 1, wherein the $F/Al_2O_3$ mole ratio is equal to or greater than 0.035.

13. The method of claim 1, wherein the template/$Al_2O_3$ mole ratio is greater than 1.5.

14. The method of claim 1, wherein the aluminophosphate or silicoaluminophosphate has the CHA framework type.

15. The method of claim 14 wherein the organic template comprises one or more dimethylamino moieties and has the following structure:

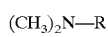

wherein R is a substituted or un-substituted aliphatic or cycloaliphatic group.

16. The method of claim 15, wherein R is a linear or branched alkyl group, a linear or branched alcohol, or a linear or branched amine.

17. The method of claim 16, wherein the alkyl group contains 1 to 12 carbon atoms, more preferably 1 to 10 carbon atoms, and most preferably 1 to 8 carbon atoms.

18. The method of claim 17, wherein the organic template is selected from one or more of the following; N,N-dimethylethanolamine, N,N-dimethylbutanolamine, N,N-dimethylheptanolamine, N,N-dimethylhexanolamine, N,N-dimethylethylenediamine, N,N-dimethylpropyelenediamine, N,N-dimethylbuytlenediamine, N,N-dimethylheptylenediamine, N,N-dimethylhexylenediamine, or dimethylethylamine, dimethylpropylamine, dimethylheptylarnine or dimethylhexylamine.

19. The method of claim 18, wherein the organic template is N,N-dimethylethanolamine, or N,N-methylpropylenediamine.

20. The method of claim 14, wherein the template is N,N-dimethylethanolamine in combination with morpholine.

21. The method of claim 14, wherein $H_2SiF_6$ and/or $[NH_4]_2SiF_6$ are used as the fluorine containing compound.

22. The method of claim 21, wherein the fluorine containing compound is added first to the reaction mixture.

23. The method of claim 21, wherein the fluorine containing compound is added last to the reaction mixture.

24. The method of claim 14, further comprising the step of calcining the crystalline molecular sieve to activate the molecular sieve of CHA framework type.

25. A process for forming a molecular sieve catalyst composition, comprising the step of forming a mixture comprising a crystalline low silica silicoaluminophosphate comprising a twinned morphology prepared by the method of claim 14, with at least one formulating agent.

26. A crystalline low silica silicoaluminophosphate molecular sieve of CHA framework type comprising a twinned morphology.

27. The crystalline low silica silicoaluminophosphate molecular sieve of CHA framework type of claim 26 in the calcined state.

28. The crystalline low silica silicoaluminophosphate molecular sieve of claim 26 having a Si/Al atomic ratio of less than 0.5, preferably less than 0.33, more preferably less than 0. 167, most preferably less than 0.1.

29. A process for forming a molecular sieve catalyst composition, comprising the step of forming a mixture comprising the crystalline low silica silicoaluminophosphate of claim 26, with at least one formulating agent.

30. A molecular sieve catalyst composition comprising at least one crystalline low silica silicoaluminophosphate as claimed in claim 26, in admixture with at least one formulating agent.

31. A hydrocarbon conversion process comprising the steps of:
(a) introducing a feedstock to a reactor system in the presence of the molecular sieve of claim 26;
(b) withdrawing from the reactor system an effluent stream; and
(c) passing the effluent gas through a recovery system recovering at least the one or more conversion products.

32. A process as claimed in claim 31 wherein the feedstock comprises one or more oxygenates.

33. A process as claimed in claim 32 wherein the one or more oxygenates comprises methanol.

34. A process as claimed in claim 31 wherein the one or more conversion products comprise one or more olefins.

35. A process as claimed in claim 34 wherein the one or more olefins comprises ethylene, propylene and mixtures thereof.

36. A process as claimed in claim 31 wherein the feedstock comprises one or more oxygenates and ammonia.

37. A process as claimed in claim 36 wherein the one or more conversion products are comprises one or more alkylamines.

38. A process as claimed in claim 37 wherein the one or more alkylamines comprises one or more methylamines.

39. A process as claimed in claim 36 wherein the one or more oxygenates comprises methanol.

40. A silicoaluminophosphate molecular sieve of CHA framework type comprising a twinned morphology and having a Si/Al atomic ratio in the range of from 0.005 to 0.17, preferably in the range of from 0.007 to 0.1, more preferably in the range of from 0.01 to 0.09, most preferably in the range of from 0.02 to 0.08.

41. A silicoaluminophosphate molecular sieve of CHA framework type comprising a twinned morphology and having a Si/Al atomic ratio in the range of from 0.005 to 0.50, preferably in the range of from 0.007 to 0.33, more preferably in the range of from 0.01 to 0.17.

* * * * *